(12) United States Patent
Niederloehner et al.

(10) Patent No.: US 10,429,464 B2
(45) Date of Patent: Oct. 1, 2019

(54) METHOD AND MAGNETIC RESONANCE APPARATUS FOR SHIMMING THE BASIC MAGNETIC FIELD BY OPERATION OF A SHIM DEVICE

(71) Applicant: Siemens Healthcare GmbH, Erlangen (DE)

(72) Inventors: Daniel Niederloehner, Erlangen (DE); Dominik Paul, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 29 days.

(21) Appl. No.: 15/902,520

(22) Filed: Feb. 22, 2018

(65) Prior Publication Data

US 2018/0238979 A1    Aug. 23, 2018

(30) Foreign Application Priority Data

Feb. 22, 2017    (DE) .......................... 10 2017 202 878

(51) Int. Cl.
*G01R 33/38*    (2006.01)
*G01R 33/387*    (2006.01)
*A61B 5/055*    (2006.01)
*G01R 33/3875*    (2006.01)

(52) U.S. Cl.
CPC ............ *G01R 33/387* (2013.01); *A61B 5/055* (2013.01); *G01R 33/3875* (2013.01)

(58) Field of Classification Search
CPC .. G01R 33/3875; G01R 33/5611; A61B 5/055
See application file for complete search history.

(56) References Cited

U.S. PATENT DOCUMENTS

| 2010/0237867 | A1* | 9/2010 | Slade | G01R 33/3873 324/314 |
| 2012/0235681 | A1* | 9/2012 | Stemmer | G01R 33/4835 324/307 |
| 2015/0054510 | A1 | 2/2015 | Biber et al. | |
| 2015/0102809 | A1* | 4/2015 | van Beek | G01R 33/443 324/309 |

* cited by examiner

*Primary Examiner* — Giovanni Astacio-Oquendo
*Assistant Examiner* — Alvaro E Fortich
(74) *Attorney, Agent, or Firm* — Schiff Hardin LLP

(57) ABSTRACT

In a magnetic resonance apparatus having a scanner that generates a basic magnetic field in an imaging volume, and an operating method to acquire data from an entirety of a recording volume, wherein the scanner has a global shim coil acting on the entire imaging volume, and a local shim coil acting, with the global shim coil, on a sub-volume containing a region of interest, a first adjustment volume is established that contains the recording volume. A smaller, second adjustment volume is established containing the region of interest, and at most, the sub-volume. Using a field map of the basic magnetic field that covers the first adjustment volume, shim currents are respectively identified for the global shim unit, for homogenizing the first adjustment volume, and for the local shim unit, for homogenizing the second adjustment volume, accounting for the effect of the first shim currents on the second adjustment volume.

11 Claims, 2 Drawing Sheets

METHOD AND MAGNETIC RESONANCE APPARATUS FOR SHIMMING THE BASIC MAGNETIC FIELD BY OPERATION OF A SHIM DEVICE

BACKGROUND OF THE INVENTION

Field of the Invention

The invention concerns a method for operating a shim device for a basic magnetic field in a magnetic resonance (MR) apparatus for imaging a region of interest within a recording area from which MR data are acquired over an entirety of the recording area. The shim device has at least one global shim unit acting on the entire imaging volume of the magnetic resonance apparatus, and the global shim coil, and at least one local shim unit, act on a sub-volume that includes the region of interest. The local shim unit has at least one local shim coil. The invention also concerns a magnetic resonance apparatus and a non-transitory, electronically readable data storage medium that implement such a method.

Description of the Prior Art

In magnetic resonance imaging, a basic magnetic field (BO field) is used in which nuclear spins of a subject are aligned. In order to generate magnetic resonance signals, excitation of these nuclear spins, produced by radio-frequency energy, causes the spins to emit signals at the Larmor frequency (magnetic resonance frequency), whereupon the decay of the excitation (relaxation) is detected. It is important that the Larmor frequencies in different spatial areas be as uniform as possible in order to be able to generate uniform excitation, and for this reason the basic magnetic field should be as homogenous as possible. Deviations in the basic magnetic field of the magnetic resonance device result in a shift of Larmor frequencies.

A magnetic resonance apparatus has a data acquisition scanner that has an imaging volume, which is also often described as a homogeneity volume. This is usually defined as the volume in which the homogeneity of the basic magnetic field is sufficient so as to enable sufficiently high-quality imaging in the different recording areas of the imaging volume.

To further improve the homogeneity of the basic magnetic field, it is known to use shim devices in the magnetic resonance apparatus. Passive shim devices, such as inserted metal parts, compensate for inhomogeneities in the apparatus structure. Active shim devices, which have shim coils are supplied with different shim currents, optimize the homogeneity specifically for certain recording areas and patients. Global shim devices are often provided with a global shim unit having global shim coils which, for example, are realized as part of the gradient coil arrangement of the magnetic resonance device which, for example, is arranged surrounding the cylindrical patient aperture. Global shim coils usually relate to the removal of interference fields, that is to say inhomogeneities, of the first order and partly of the second order (with regard to spherical harmonics). Global shim coils of the third order have also been proposed, in particular for ultra-high field systems. It has been established that for certain applications, in particular in certain body regions of a patient from which MR data are to be acquired, these global shim coils are insufficient to enable adequate homogenization of the basic magnetic field. The nape of the neck (cervical spine) or the chest, for example, represents such body regions.

To remedy this problem and therefore enable better homogenization of the basic magnetic field in critical body regions, the use of local shim coils has been proposed. Such local shim coil units, which are placed close to the patient and only influencing small effective ranges can have local coils which, in the case of such imaging tasks, are in any case used for transmitting and/or receiving radio frequency pulses/magnetic resonance signals. These local coil arrangements are placed very close to the body of the patient, for example at a distance of a few centimeters. Local shim coils can, for example, have an extent of a few tens of centimeters. In contrast, global shim coils are at a greater distance from the patient and/or object of investigation, generally speaking, and have a greater extent on the order of one meter.

Consequently, the spatial extent of the shim fields of local shim coils, that is to say the spatial extent of the effective range of the local shim coils, is very limited, such that they can also be referred to as "small-volume" or "sub-volume" shim coils. In this case, the effective range is suitably defined such that technically feasible influence for homogenization is possible therein.

To ascertain the shim currents for a particular imaging task, which is usually characterized by a region of interest (ROI) in a recording area, usually an adjustment volume is first defined in which the optimization should be effective. The adjustment volume can be defined such that the recording area is contained therein. Then a basic magnetic field map (BO map) is determined at least for the adjustment volume. Many methods for generating such a BO map are known in the prior art. Usually the phase shift, which occurs on the basis of different Larmor frequencies in different spatial regions, is measured. The deviation of the Larmor frequencies from each other is a measure of the basic magnetic field difference between the spatial regions. Since the shim currents were known during the measurement of the basic magnetic field map, on the basis of the known generated shim fields for the shim coils, a combination of shim fields can now be ascertained in an optimization method such that an optimum possible homogeneity in the adjustment volume is given. For example, the solution of a system of equations can be sought and/or a simulation can be performed.

However, it has been shown that problems occur when ascertaining the shim currents if shim devices are used that have both a global shim unit and a local shim unit. The different spatial extents of the effective ranges of the global shim coils and the local shim coils result in instability problems during calculations when a large adjustment volume is used. While the global shim coils have a broad effective range that usually encompasses the entire imaging volume, the local shim coils operate only in a limited effective range. A joint calculation of the shim currents on an adjustment volume therefore can lead to false and/or sub-optimal results. In particular, when the adjustment volume is significantly greater than the effective range of the local shim coils, the advantage of the local shim coils can no longer be fully utilized.

In order to solve this problem, restricting the adjustment volume to small extents has been proposed, typically to the effective range of the local shim coils that includes the region of interest, but not the entire recording area for which magnetic resonance data are recorded. The problem thus arises that beyond the adjustment volume the image quality can suffer greatly, because optimization takes place in the adjustment volume at the expense of homogeneity beyond the adjustment volume.

SUMMARY OF THE INVENTION

An object of the invention is to provide an improved utilization of local shim coils while still ensuring sufficient homogenization in the recording area.

To solve this problem, in the method according to the invention, a first adjustment volume is established in a computer, this first adjustment volume including at least the recording area. A smaller second adjustment volume is established in the computer that includes at least the region of interest, and as a maximum, the sub-volume. A first basic magnetic field map is measured with the magnetic resonance scanner, which covers at least the first adjustment volume. Using the basic magnetic field map, the computer identifies first shim currents for the global shim coils for the homogenization of the first adjustment volume, and second shim currents for the local shim coils for the homogenization of the second adjustment volume, taking into account the effect of the first shim currents on the second adjustment volume. The computer determines control signals for operating respective amplifiers that feed the global shim coils and the local shim coils, the control signals causing those respective amplifiers to feed the global shim coils and the local shim coils with the respectively determined shim currents during operation of the scanner, in order to acquire magnetic resonance data from the region of interest of the subject.

A multi-stage procedure therefore is implemented according to the invention in which two different adjustment volumes are defined, namely a first adjustment volume that is chosen to be large and includes the entire recording area, and a second adjustment volume, which is local and relates to the region of interest and the effective range of the local shim coils, that is to say the sub-volume. In the example of imaging of the nape of the neck of a person, the first adjustment volume, for example including the head, the neck and the shoulders, can be established, but the second adjustment volume is restricted to the nape of the neck itself. In this case, the first shim currents are calculated for the global shim coils for the homogenization of the first adjustment volume, that is to say in particular comprising the entire recording area. The second shim currents for the local shim coils are determined in a restricted view of the second adjustment volume and take into account the effect of the first shim currents. A stable calculation method taking into account the effective ranges of the shim coils is thereby created for shim currents with the combined use of local and global shim coils, leading to an improvement and/or maintenance of the global image quality when optimizing the local basic magnetic field homogeneity in the region of interest. Additional adjustment measurements are avoided.

In an embodiment of the present invention, the first shim currents are first determined within the context of a first optimization method with regard to the homogeneity of the basic magnetic field in the first adjustment volume. A second basic magnetic field map taking into account the first shim currents, is then calculated for the second adjustment volume from the first basic magnetic field map, and is used as the basis for determining the second shim currents within the context of a second optimization method with regard to the homogeneity of the basic magnetic field in the second adjustment volume. In this case, homogenization therefore ultimately takes place gradually, wherein homogenization is initially undertaken in the greater first adjustment volume, the effects of which on the basic magnetic field distribution in the second adjustment volume are calculated by determining an updated, second basic magnetic field map and then optimization takes place for the second adjustment volume. This is an extremely robust procedure since only a specific adjustment volume of the adjustment volumes is ever optimized. The target function of the respective optimization then refers to maximum homogeneity in the corresponding adjustment volume, wherein the shim currents are regarded as optimization parameters. In this case, it is pointed out that in such an embodiment it is also entirely feasible to undertake a subsequent adaptation of first shim currents for the global shim coils after the determination of the second shim currents has been completed, by seeking an iterative procedure and the gradual procedure is therefore run through a plurality of times.

In another embodiment of the present invention, the first and second shim currents are determined in a joint optimization method, wherein the optimization with regard to the homogeneity of the basic magnetic field in the first adjustment volume and the optimization with regard to the homogeneity of the basic magnetic field in the second adjustment volume are weighted, as optimization objectives, by weighting values which can be selected by the user. A comparable result to the aforementioned multi-stage procedure can also be obtained by an optimization algorithm receiving both adjustment volumes as inputs and the corresponding optimization method for optimizing the basic magnetic field homogeneity on the large adjustment volume using only the shim currents for the global shim coils, and for optimization in the small adjustment volume, using only the shim currents for the local shim coils. A target function can then be formulated in which weighting factors can be used to establish which of the adjustment volumes the homogenization should primarily focus. In other words, it is possible to control the influence of the two adjustment volumes on the final result using the weighting factors, wherein the weighting factors can be modifiable, particularly in a user-defined manner, so as to allow a flexible weighting onto the adjustment volumes. Thus, for example, in imaging tasks in which the anatomy surrounding the region of interest is irrelevant, a greater weighting can be placed on the region of interest than in cases in which the anatomy in the region of interest is to be considered in the context of the anatomy beyond the region of interest, which also needs to be presented in sufficient quality. Through simultaneous consideration/optimization, a kind of interaction also occurs between the optimization processes in which the respective shim currents can be mutually adapted to each other to achieve the desired overall result, which is particularly determined by the weighting factors. Nonetheless, in this embodiment it is also essential that a strict distinction be drawn between the adjustment volumes and the respective relevant optimization parameters.

It should also be noted that, in further embodiments, boundary conditions can be formulated, for example, to require that the homogeneity in a specific adjustment volume of the adjustment volumes does not fall below a certain value and the like.

A general development of the present invention provides that the first adjustment volume is established independent of the user, in particular as the entire imaging volume of the magnetic resonance device. It is therefore possible that the first adjustment volume need not necessarily be determined on the basis of user inputs but that a standardized large adjustment volume can also be used which covers virtually all the applications or at least many applications. Then no information in this regard need be requested from the user. However, it is also conceivable to use, for example, an envelope for the recording area or the like known on account of user inputs, for example a choice of protocol.

On the other hand, it is expedient if at least the second adjustment volume is determined as a function of a user input describing the region of interest, in particular. In this case, it is entirely conceivable that the second adjustment volume is explicitly chosen by a user within the aforementioned predefined limits on the basis of a graphical representation, for example on the basis of an overview image; however, it is also possible and preferable to evaluate other user inputs, for example those available in a radiology information system and/or a hospital information system and which describe the imaging task more precisely, in particular also describe the diagnostic issue and thus the region of interest, or those which describe the region of interest in more detail through the choice of protocol or the like. For example, if local shim coils provided in local coil arrangements are used, the determination of the second adjustment volume can also include positioning information with regard to the local shim coils. For example, neck coils are known as local coil arrangements which can be positioned beneath the patient on the patient table. The goal is preferably to avoid having to request any further user input beyond what is necessary so as to facilitate the execution of the method "in the background". Therefore, existing user inputs already effected and possibly also information on the magnetic device side are preferably used.

Specifically, it can be provided that the global shim unit is designed to compensate for basic magnetic field inhomogeneities of at least the first and second order and/or is installed in a gradient coil arrangement of the magnetic resonance device and/or the local shim unit is designed as part of a local coil arrangement. In this case, higher orders than the first and second order are available with regard to spherical harmonics, particularly for magnetic resonance devices with a particularly high basic magnetic field, for example of 7 T or higher. The global shim coils can be installed in a gradient coil arrangement which in particular is arranged surrounding the cylindrical patient aperture. As far as the local shim coils are concerned, these can be integrated in a local coil arrangement. Approaches have also been proposed in which at least one local coil element of the local coil is used as at least one of the local shim coils, wherein it is also equally possible, however, to provide the local shim coils in addition to the local coil elements which are used for transmitting and/or receiving.

In addition to the method, the present invention concerns a magnetic resonance apparatus having a scanner which, in addition to the shim device already described, also has a control computer designed to execute the method according to the invention. The control computer can have a determination processor to determine the adjustment volumes, a measuring processor to measure the first basic magnetic field map, and an identification processor to identify the first and second shim currents. The computer determines control signals for operating respective amplifiers that feed the global shim coils and the local shim coils, the control signals causing those respective amplifiers to feed the global shim coils and the local shim coils with the respectively determined shim currents during operation of the scanner, in order to acquire magnetic resonance data from the region of interest of the subject.

All the embodiments with regard to the method according to the invention are applicable to the magnetic resonance apparatus according to the invention, which therefore has the aforementioned advantages.

The present invention also encompasses a non-transitory, computer-readable data storage medium encoded with programming instructions that, when the storage medium is loaded into a computer of a magnetic resonance apparatus, cause the computer to operate the magnetic resonance apparatus so as to implement any or all embodiments of the method according to the invention, as described above.

DESCRIPTION OF THE PREFERRED EMBODIMENTS

Figure 1:
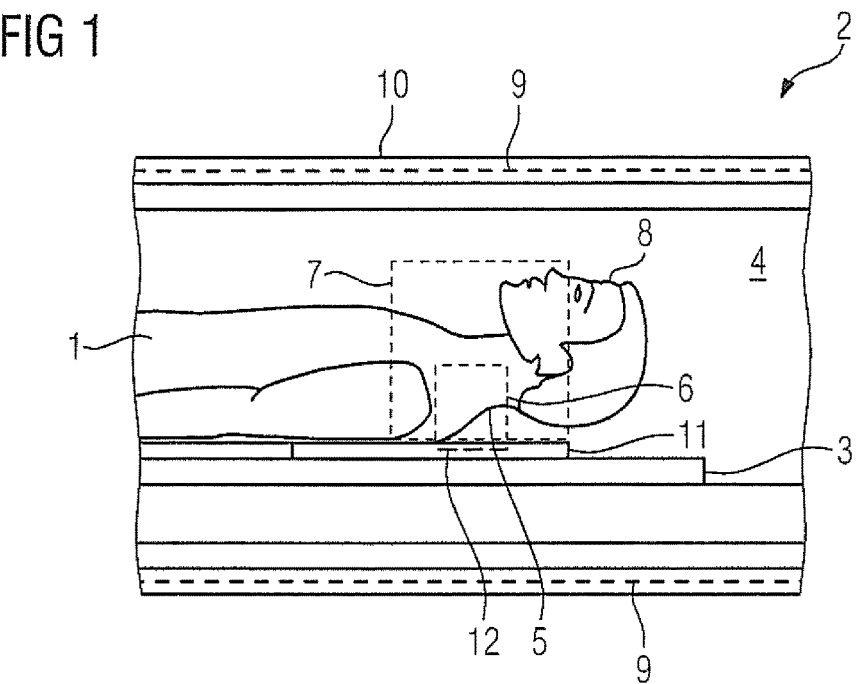
FIG. 1 illustrates an imaging task in a magnetic resonance device.

FIG. 1 schematically shows an imaging procedure for a patient 1 in a magnetic resonance scanner 2 (only partially shown) of a magnetic resonance apparatus. The patient 1 has been moved into a patient aperture 4 of the magnetic resonance scanner 2 by a patient table 3. The target of the imaging in the present case is the nape of the neck 5 of the patient 1, which is marked by a region of interest 6 indicated by dotted lines. However, the MR data acquisition to be carried out extends to a recording area 7, which also contains parts of the head 8 and the shoulders of the patient 1.

To improve the image quality of the resulting magnetic resonance data, the magnetic resonance scanner 2 has a shim device with two shim units. One global shim unit uses global shim coils 9 only schematically indicated, which can affect the entire imaging volume, that is to say the homogeneity volume, of the magnetic resonance scanner 2, and which are installed in a gradient coil arrangement 10 which extends around the patient aperture 4. The corresponding gradient coil elements are not shown, for clarity.

However, the shim device also has a second, local shim unit, which in this case is formed as a local coil arrangement 11, in this case a neck coil, onto which the patient 1 was placed. In addition to local coil elements (not shown in more detail here for clarity), the local coil arrangement 11 thus comprises indicated local shim coils 12 which are significantly smaller than the global shim coils 9 and accordingly have a smaller effective range in each case. The totality of the effective ranges is referred to as a sub-volume covered by the local shim coils 12. For simplicity, the sub-volume corresponds to the region of interest 6 (ROI) in this case. The region of interest 6 and the sub-volume are therefore smaller than the recording area 7.

With the exemplary embodiments of the method according to the invention shown below, shim currents can be identified for the global shim coils 9 and the local shim coils 12. For example, eight global shim coils 9 and/or shim channels and two local shim coils 12 and/or shim channels can be provided such that a required high image quality exists in the region of interest 6 on account of high basic magnetic field homogeneity, and yet the quality of the magnetic resonance data beyond the region of interest 6 in the recording area 7 is high enough to identify and assess relevant anatomical structures and thus also achieve sufficient homogeneity there.

Figure 2:
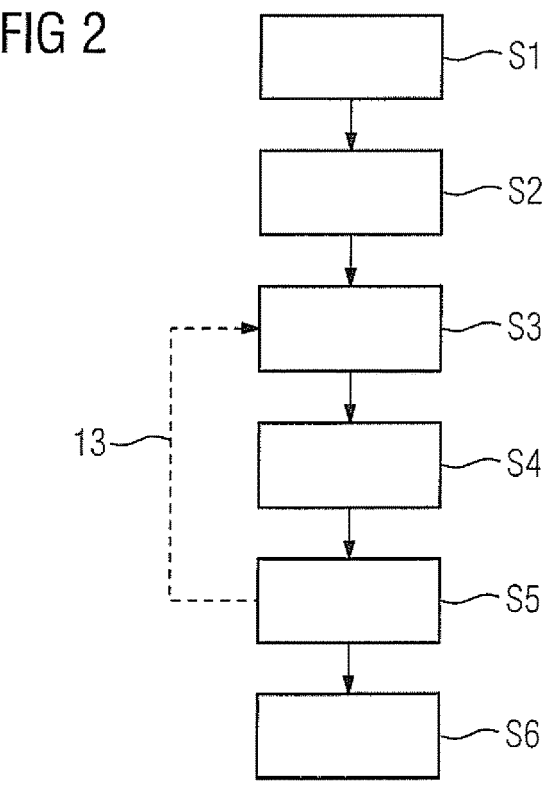
FIG. 2 is a flowchart of a first exemplary embodiment of the method according to the invention.

In a step S1 of the first exemplary embodiment of the method according to the invention shown according to FIG. 2, two adjustment volumes are first established. A first, large adjustment volume comprises at least the recording area 7 in this case and can be established in advance, for example as the imaging volume (homogeneity volume) of the magnetic resonance scanner 2 overall or at least as an area which covers as many applications and thus recording areas 7 as possible. The second adjustment volume in this case is selected as the region of interest 6 and therefore also the sub-volume, and therefore comprises the effective ranges of the local shim coils 12 and is significantly smaller than the first adjustment volume. The second adjustment volume can be selected expediently on the basis of a user input describing at least the region of interest 6.

In a step S2, in a measuring range comprising at least the first adjustment volume, a first basic magnetic field map is ascertained using a common measurement method for such basic magnetic field maps (B0 maps). This naturally takes place under defined, known shim conditions that is to say with known measurement shim currents which can also be zero.

On the basis of this first basic magnetic field map, in a step S3 first shim currents are now determined for the global shim coils 9 in an optimization method pertaining to the first adjustment volume which lead to the best possible homogenization of the basic magnetic field in the first adjustment range. With the first shim currents obtained as a result, in step S4 a second basic magnetic field map is determined which at least describes these first shim currents and/or the corresponding effect of the global shim coils 9 in the second adjustment volume.

On this basis, in step S5 in a second optimization method, limited to the second adjustment volume, it is then possible to determine second shim currents (here only for the local shim coils 12) which ensure the best possible homogenization in the second adjustment volume.

If a renewed adaptation of the first shim currents based thereon is to take place, it is conceivable to choose an iterative procedure, as indicated by the dashed arrow 13. Of course, a first basic magnetic field map updated with the first and second shim currents is assumed, such that during optimization in the following iteration steps correction currents for the already determined first and second shim currents emerge.

In a step S6, the finally determined first and second shim currents are then applied in the imaging in order to ensure homogenization in the recording area 7 and in the region of interest 6.

Figure 3:
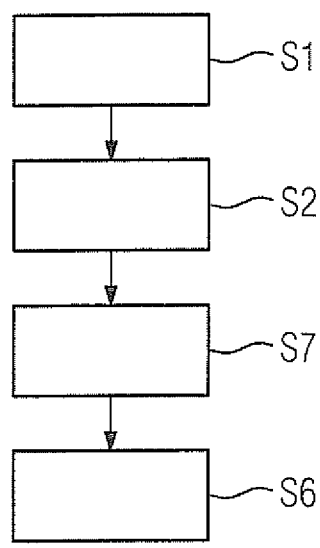
FIG. 3 is a flowchart of a second exemplary embodiment of the method according to the invention.

FIG. 3 illustrates an alternative embodiment of the method according to the invention. In this case, the steps S1 and S2 correspond to those of the exemplary embodiment according to FIG. 2, but in a following step S7 a joint determination of optimized first and second shim currents is carried out in a joint optimization method, that is to say using a joint optimization algorithm. For this purpose, an adaptation of the first shim currents for the global shim coils as optimization parameters only takes place for the first adjustment volume, an adaptation of second shim currents for the local shim coils 12 only with regard to the second adjustment volume, wherein weighted as the objective function by weighting factors, both the homogeneity of the basic magnetic field in the first adjustment volume and the homogeneity of the basic magnetic field in the second adjustment volume are taken into account. The weighting factors can be predefined, but are preferably selectable by the user. In this way, within joint optimization, a mutual tuning of first and second shim currents takes place to achieve an optimum result in terms of the weighting factors, although for optimization on the first adjustment volume only the first shim currents are used for the global shim coils, and for optimization on the smaller second adjustment volume only the second shim currents for the local shim coils 12.

The following step then again corresponds to the step S6, in which the identified first and second shim currents are applied.

Figure 4:
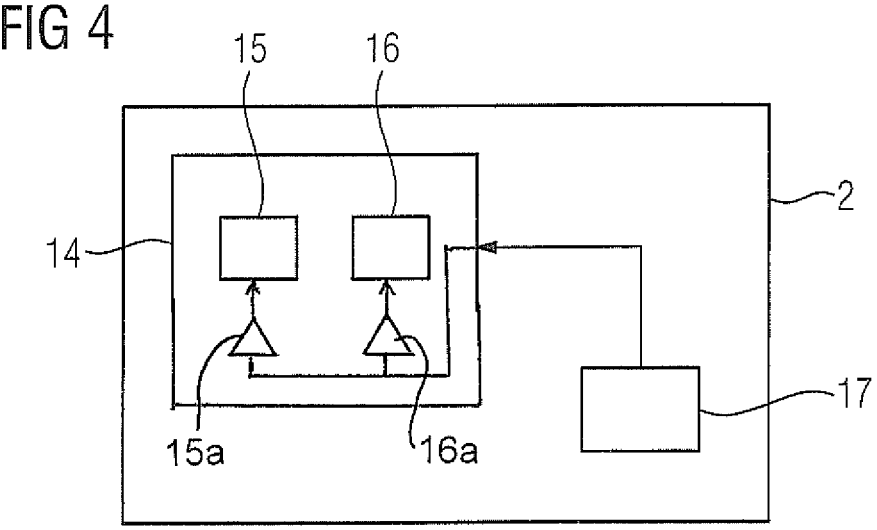
FIG. 4 schematically illustrates a magnetic resonance apparatus according to the invention.

FIG. 4 finally shows the relevant components of the magnetic resonance scanner 2 according to the invention in more detail in the form of a highly simplified schematic diagram. This comprises, as aforementioned, the shim device 14, which in turn comprises the first shim unit 15 with the global shim coils 9 and the second shim unit 16 with the local shim coils 12. The operation of the magnetic resonance scanner 2, in particular therefore also the shim device 14, is controlled by a control device 17 of the magnetic resonance scanner 2 which is designed to execute the method according to the invention.

The computer 17 determines control signals for that are provided to and operate respective amplifiers 15a and 16a that feed the global shim coils 9 in the shim unit 15 and the local shim coils 12 in the shim unit 16, the control signals causing those respective amplifiers 15a and 16a to feed the global shim coils 9 and the local shim coils 12 with the respectively determined shim currents during operation of the scanner 2, in order to acquire magnetic resonance data from the region of interest of the subject.

For this purpose, in addition to conventional components in particular, the control computer 17 can have a sequencer for playing out magnetic resonance sequences and a read-out processor for receiving magnetic resonance signals, as well as a determination processor for determining the first and the second adjustment volumes, a measuring processor for establishing the first basic magnetic field map, an identification processor for identifying the shim currents, and a control processor for controlling the amplifiers of the shim device 14.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for operating a magnetic resonance (MR) apparatus that comprises an MR data acquisition scanner having a basic field magnet that generates a basic magnetic field in an imaging volume of the scanner, and a global shim unit that acts on an entirety of said imaging volume in order to homogenize the basic magnetic field therein, and said scanner having a local shim unit that acts on a sub-volume comprising a region of interest, together with said global shim unit, said method comprising:

in a computer, establishing a first adjustment volume that comprises a recording volume, wherein MR data are to be acquired with said scanner in an entirety of said recording volume;

in said computer, establishing a second adjustment volume, which is smaller than said first adjustment volume, said second adjustment volume comprising at least said region of interest and, as a maximum, said sub-volume;

with said computer, operating said scanner in order to obtain a field map of said basic magnetic field at least within said first adjustment volume;

in said computer, using said field map to determine first shim currents for said global shim coils that cause homogenization of said basic magnetic field in said first adjustment volume, and to determine second shim currents for said local shim coils that cause homogenization of said basic magnetic field in said second adjustment volume, taking into account an effect of said first shim currents on said second adjustment volume; and in said computer, generating control signals in order to operate respective amplifiers that feed said global shim coils and said local shim coils so as to supply said global shim coils with said first shim currents and to supply said local shim coils with said second shim currents, while operating said scanner in order to acquire MR data from said recording volume.

2. A method as claimed in claim 1 wherein said field map is a first field map, and wherein said method comprises:

in said computer, determining said first shim currents by executing a first optimization algorithm with regard to the homogeneity of the basic magnetic field in the first adjustment volume; and in said computer, calculating a second field map for said second adjustment volume from said first field map, by also taking into account said first shim currents, and using said second field map to determine said second shim currents by executing a second optimization algorithm with regard to homogeneity of the basic magnetic field in the second adjustment volume.

3. A method as claimed in claim 1 comprising, in said computer, determining said first and second shim currents by executing a joint optimization algorithm, wherein optimization with regard to the homogeneity of the basic magnetic field in the first adjustment volume and optimization with regard to the homogeneity of the basic magnetic field in the second adjustment volume are weighted respectively as optimization objectives, with weighting values.

4. A method as claimed in claim 1 comprising manually entering inputs representing said weighting values into said computer.

5. A method as claimed in claim 1 comprising establishing said first adjustment volume to encompass an entirety of the imaging volume of the scanner.

6. A method as claimed in claim 1 comprising establishing said second adjustment volume dependent on a user entry that describes said region of interest.

7. A magnetic resonance (MR) apparatus comprising:

an MR data acquisition scanner comprising a basic field magnet that generates a basic magnetic field in an imaging volume of the scanner, a global shim unit that acts on an entirety of said imaging volume with at least one global shim coil, and a local shim unit that acts on a sub-volume, comprising a region of interest of a subject, with at least one local shim coil together with said global shim unit, said global shim unit comprising a global shim amplifier that supplies said at least one global shim coil and said local shim unit comprising a local shim amplifier that supplies said at least one local shim coil;

a computer configured to establish a first adjustment volume that comprises a recording volume, wherein MR data are to be acquired with said scanner in an entirety of said recording volume;

said computer being configured to establish a second adjustment volume, which is smaller than said first adjustment volume, said second adjustment volume comprising at least said region of interest and, as a maximum, said sub-volume;

said computer being configured to operate said scanner in order to obtain a field map of said basic magnetic field at least within said first adjustment volume;

said computer being configured to use said field map to determine first shim currents for said global shim coils that cause homogenization of said basic magnetic field in said first adjustment volume, and to determine second shim currents for said local shim coils that cause homogenization of said basic magnetic field in said second adjustment volume, taking into account an effect of said first shim currents on said second adjustment volume; and said computer being configured to generate respective control signals in order to operate said global shim amplifier to feed said global shim coils and said local shim amplifier to feed said local shim coils, so as to supply said global shim coils with said first shim currents and to supply said local shim coils with said second shim currents, while operating said scanner in order to acquire MR data from said recording volume.

8. A magnetic resonance apparatus as claimed in claim 7 wherein said global shim unit is designed to compensate for inhomogeneities in said basic magnetic field of at least the first and second orders.

9. An MR apparatus as claimed in claim 7 wherein said scanner comprises a gradient coil arrangement and wherein said at least one global shim coil of said global shim unit is installed in said gradient coil arrangement.

10. An MR apparatus as claimed in claim 7 wherein said scanner comprises a local coil arrangement, and wherein said at least one local coil of said local shim unit is used as at least one coil of said local coil arrangement.

11. A non-transitory, computer-readable data storage medium encoded with programming instructions, said storage medium being loaded into a computer of a magnetic resonance (MR) apparatus that comprises an MR data acquisition scanner comprising a basic field magnet that generates a basic magnetic field in an imaging volume of the scanner, a global shim unit that acts on an entirety of said imaging volume with at least one global shim coil, and a local shim unit that acts on a sub-volume, comprising a region of interest of a subject, with at least one local shim coil together with said global shim unit, said global shim unit comprising a global shim amplifier that supplies said at least one global shim coil and said local shim unit comprising a local shim amplifier that supplies said at least one local shim coil, said programming instructions causing said computer to:

establish a first adjustment volume that comprises a recording volume, wherein MR data are to be acquired with said scanner in an entirety of said recording volume;

establish a second adjustment volume, which is smaller than said first adjustment volume, said second adjustment volume comprising at least said region of interest and, as a maximum, said sub-volume;

operate said scanner in order to obtain a field map of said basic magnetic field at least within said first adjustment volume;

use said field map to determine first shim currents for said global shim coils that cause homogenization of said basic magnetic field in said first adjustment volume, and to determine second shim currents for said local shim coils that cause homogenization of said basic magnetic field in said second adjustment volume, taking into account an effect of said first shim currents on said second adjustment volume; and generate respective control signals in order to operate said global shim amplifier to feed said global shim coils and said local shim amplifier to feed said local shim coils, so as to supply said global shim coils with said first shim currents and to supply said local shim coils with said second shim currents, while operating said scanner in order to acquire MR data from said recording volume.

\* \* \* \* \*